United States Patent
Behrens et al.

(10) Patent No.: US 11,376,198 B2
(45) Date of Patent: Jul. 5, 2022

(54) POWDER CONTAINING CRYSTALS COMPRISING INGREDIENTS ENCLOSED THEREIN

(71) Applicant: SYMRISE AG, Holzminden (DE)

(72) Inventors: Kolja Behrens, Polle (DE); Patrick Ott, Holzminden (DE); Nicolas Pichon, Lüchtringen (DE); Nadine Schmidtmeier, Lügde (DE); Jörn Wiedemann, Holzminden (DE)

(73) Assignee: SYMRISE AG, Holzminden (DE)

( * ) Notice: Subject to any disclaimer, the term of this patent is extended or adjusted under 35 U.S.C. 154(b) by 64 days.

(21) Appl. No.: 16/619,576

(22) PCT Filed: Jun. 7, 2017

(86) PCT No.: PCT/EP2017/063839
§ 371 (c)(1),
(2) Date: Dec. 5, 2019

(87) PCT Pub. No.: WO2018/224142
PCT Pub. Date: Dec. 13, 2018

(65) Prior Publication Data
US 2020/0129385 A1    Apr. 30, 2020

(51) Int. Cl.
| | | |
|---|---|---|
| *A61K 8/02* | (2006.01) | |
| *A61K 8/20* | (2006.01) | |
| *A61K 8/23* | (2006.01) | |
| *A61K 8/60* | (2006.01) | |
| *A61K 8/73* | (2006.01) | |
| *A61K 8/87* | (2006.01) | |
| *A61K 8/88* | (2006.01) | |

(52) U.S. Cl.
CPC .............. *A61K 8/022* (2013.01); *A61K 8/20* (2013.01); *A61K 8/23* (2013.01); *A61K 8/60* (2013.01); *A61K 8/733* (2013.01); *A61K 8/87* (2013.01); *A61K 8/88* (2013.01); *A61K 2800/59* (2013.01); *A61K 2800/805* (2013.01)

(58) Field of Classification Search
None
See application file for complete search history.

(56) References Cited

U.S. PATENT DOCUMENTS

| 4,371,029 A * | 2/1983 | Lindner ................ F28D 20/025 |
|---|---|---|
| | | 165/111 |
| 2006/0110442 A1 * | 5/2006 | Wonschik ............... A23L 27/72 |
| | | 424/451 |
| 2016/0303006 A1 | 10/2016 | Popplewell et al. |

FOREIGN PATENT DOCUMENTS

| CN | 1917945 A | 2/2007 |
|---|---|---|
| CN | 104936573 A | 9/2015 |
| CN | 105050705 A | 11/2015 |
| WO | 2008065563 A1 | 6/2008 |
| WO | WO 2008065563 A1 | 6/2008 |
| WO | 2014047496 A2 | 3/2014 |
| WO | 2014085286 A1 | 6/2014 |

OTHER PUBLICATIONS

Choi et al., "Preparation and characterization of microcapsules containing perfumes with different polymer shells", Theories and Applications of Chem. Eng, 8(2), 2002, pp. 2493-2496. (Year: 2002).*
International Search Report and Written Opinion dated Oct. 23, 2017 for corresponding PCT Application No. PCT/EP2017/063839.
Chinese Office Action and English translation dated Mar. 21, 2022 for corresponding Chinese Application No. 201780091808.7.

* cited by examiner

*Primary Examiner* — Melissa L Fisher
(74) *Attorney, Agent, or Firm* — Polsinelli PC

(57) ABSTRACT

The present invention primarily relates to a method for producing a powder containing a plurality of capsules incorporated into crystals, wherein these capsules contain one or more ingredients. Further, the present invention relates to the respective powder, as well as product containing this powder, the use of the powder as well as methods for producing respective products and methods for perfuming substrates.

13 Claims, 2 Drawing Sheets

1 untreated
2 kneaded
3 rubbed

POWDER CONTAINING CRYSTALS COMPRISING INGREDIENTS ENCLOSED THEREIN

CROSS-REFERENCE TO RELATED APPLICATIONS

This application is a national stage application (under 35 U.S.C. § 371) of PCT/EP2017/063839, filed Jun. 7, 2017, which is incorporated herein by reference in its entirety.

The present invention primarily relates to a method for producing a powder consisting of or comprising a plurality of capsules enclosed in crystals and containing one or more ingredients.

The invention further relates to such a powder, consisting of or comprising a plurality of capsules enclosed in crystals and containing one or more ingredients, furthermore product comprising such a powder, the use of such a powder and methods for perfuming of substrates.

Further aspects and preferred embodiments of the present invention result from the following specification, the attached examples and particularly the attached claims.

The incorporation of capsules, e.g. capsules containing perfume oil, into washing powder may be for example performed by spraying capsules onto the finished washing powder. However, in this case, the capsules are unprotected and the probability of grinding a part of the capsules during the further production process (e.g. mixing and conveying the powder) by arising shear forces in the washing powder is very high. As far as the capsules do not sufficiently attach to the particles of the washing powder, a separation of the capsules in the powder may also occur. Thus, the distribution of the capsules in the washing powder is no longer uniform. A further method to incorporate capsules into washing powder is to spray dry the capsules together with the other components of the washing powder. However, in this way, a strong thermal pressure is applied to the capsules. By this thermal pressure, there is the risk of changing the quality of or even destroying the used capsules.

The primary object of the present invention was thus to provide a method for producing a powder in which the above mentioned disadvantages are not or only partly present. Further aspects of this object as well as further objects result from the following remarks.

The primary object is solved according to the invention by a method for producing a powder consisting of or comprising a plurality of capsules (K) enclosed in crystals and containing one or more ingredients, comprising or consisting of the following steps:

(i) providing one or more solvents,
   providing one or more crystallisable materials and
   providing one or more capsules (K) containing one or more ingredients,
(ii) optionally: increasing the temperature of the solvent(s),
(iii) adding
   (iii.1) the provided crystallisable material(s) and
   (iii.2) optionally: the provided capsules (K) before, after or simultaneously with the crystallisable material(s),
   to the solvent(s) and solving the provided crystallisable material(s) in the solvent(s) to obtain a mixture (M1),
(iv) reducing the temperature of the mixture (M1) to a temperature below or even with the crystallization of the provided crystallisable material(s),
(v) adding the provided capsules (K) or, respectively, further capsules (K), wherein step (v) is optional in case step (iii.2) is applied,
(vi) further reduction of the temperature of the mixture (M1) to obtain a mixture (M2) comprising a plurality of capsules (K) enclosed in crystals and containing one or more ingredients,
(vii) collecting the capsules (K) enclosed in crystals and containing one or more ingredients.

Figure 1:
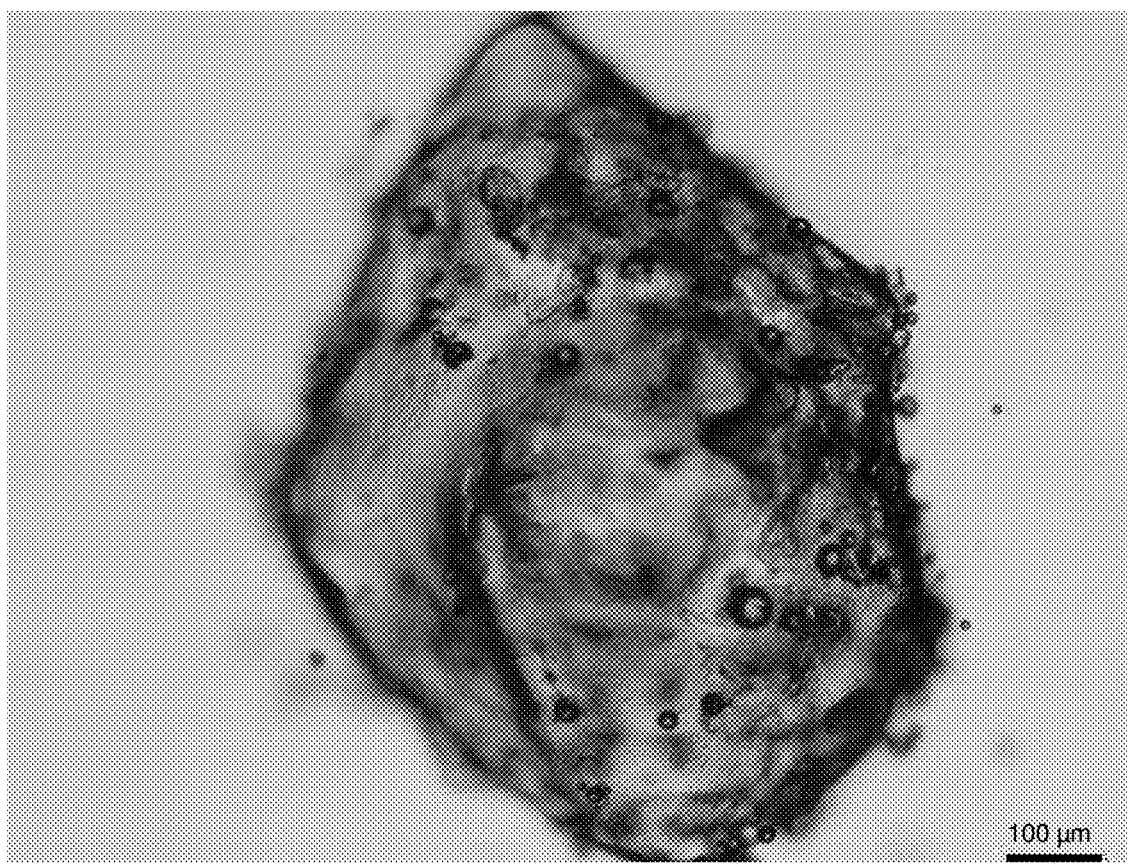
FIG. 1 is an image of a capsule (K) at least partly enclosed by crystals.

The capsules (K) are at least partly enclosed by and/or in the forming crystals during the process of crystallization (cf. FIG. 1).

Preferably, the crystallisable material(s) are present in a concentration in the solvent(s) which allows the initiation of the crystallization at a temperature which is higher than the freezing point of the solvent(s).

The capsules (K) enclosed in crystals and containing one or more ingredients provided in step (i) may be present as powder, in a dispersion or in other form.

The initiation of the crystallization is understood as the time point at which first crystals are visibly be eye when observing the mixture M1.

Preferably, step (v) is immediately performed after step (iv) in a method according to the invention.

The crystals or, respectively, a powder produced according to the invention can be advantageously mixed without problems with finished washing powder formulations or, respectively, typical components of a washing powder. In this case, the contained or, respectively, enclosed capsules are better protected from mechanical stress when incorporated into the washing powder that capsules which are loosely incorporated into the washing powder.

In case of necessity, the particle size of the crystals produced according to the invention may be adapted to the particle size of the washing powder by adjusting the respective parameters (e.g. temperature or, respectively, temperature profile during the process and the process duration) such that separation phenomena are avoided in the washing powder composition.

Furthermore, strongly thermal stress as e.g. occurring during spray drying are avoided.

Due to the fact that the product produced according to the invention is a powder, the necessary effort in transport and packaging is reduced compared to e.g. liquid capsule dispersions.

The capsules (K) enclosed in crystals and containing one or more ingredients provided in step (i) may for example contain one or further aromatic substances:

Aromatic substances to be preferably used according to the invention comprise for example perfume oils which are or will be for example composed of the following raw substances:

Extracts of natural substances such as essential oils, Concretes, Absolues, Resins, Resinoids, Balms, tinctures such as e.g. Ambra tincture; Amyris oil; Angelica seed oil; Angelica root oil; Anise oil; valerian oil; Basil oil; tree moss absolue; Bay oil; mugwort oil; Benzoe resin; Bergamot oil; beeswax Absolue; birch tar oil;

Bitter almond oil; savoury oil; Bucco leaf oil; Cabreuva oil; Cade oil; Calmus oil; Campher oil; Cananga oil; Cardamomen oil; Cascarilla oil; Cassia oil; Cassie absolue; Castoreum absolue; cedar leaf oil; cedar wood oil; Cistus oil; Citronell oil; lemon oil; Copaiva balm; Copaiva balm oil; Coriander oil; Costus root oil; Cumin oil; Cypress oil; Davana oil; dill weed oil; Dill seed oil; Eau de brouts absolue; oak moss Absolue; Elemi oil; Estragon oil; Eucalyptus citriodora-oil; Eucalyptus oil; Fennel oil; spruce needle oil; Galbanum oil; Galbanumresin; Geranium oil; Grapefruit oil; Guajak wood oil; Gurjun balm; Gurjunalsam oil; Helichrysum absolue; Helichrysum oil; ginger oil; iris root Absolue; Iris root oil; Jasmin absolue; Kalmus oil; chamomile oil blue; chamomile oil roman; carrot seed oil; Kaskarilla oil; jaw needle oil; spearmint oil; caraway oil; Labdanum oil; Labdanum absolue; Labdanumresin; Lavandin absolue; Lavandin oil; Lavender absolue; Lavender oil; Lemongras oil; lovage oil; Lime oil distilled; Lime oil pressed; Linaloe oil; Litsea-cubeba-oil; laurel leaf oil; Macis oil; Majoran oil; Mandarin oil; Massoirinden oil; Mimosa absolue; musk corn oil; musk tincture; Muskatel-Sage-oil; nutmeg oil; Myrrh absolue; Myrrh oil; Myrten oil; carnation leaf oil; carnation blossom oil; Neroli oil; Olibanum absolue; Olibanum oil; Opopanax oil; orange blossom Absolue; Orange oil; Origanum oil; Palmarosa oil; Patchouli oil; Perilla oil; Perubalm oil; parsley oil; parsley seed oil; Petitgrain oil; peppermint oil; pepper oil; Piment oil; Pine oil; Poley oil; Rose absolue; rose wood oil; Rose oil; Rosemary oil; sage oil dalmatinic; sage oil spanish; Sandal wood oil; celery seed oil; Spiklavender oil; Star anise oil; Styrax oil; Tagetes oil; pine tree needle oil; Tea-tree-oil; Terpentin oil; Thyme oil; Tolubalm; Tonka absolue; Tuberosen absolue; Vanilla extract; violet leaf Absolue; Verbena oil; Vetiver oil; juniper berry oil; wine yeast oil; wormwood oil; wintergreen oil; Ylang oil; Ysop oil; Zibet absolue; cinnamon leaf oil; cinnamon bark oil as well as fractions thereof or, respectively ingredients isolated thereof;

single aromatic substances of the group of carbohydrates such as e.g. 3-Carene; alpha-Pinene; beta-Pinene; alpha-Terpinene; gamma-Terpinene; p-Cymol; Bisabolen; Camphen; Caryophyllen; Cedren; Farnesen; Limonene; Longifolen; Myrcen; Ocimen; Valencen; (E,Z)-1,3,5-Undecatrien; styrene; Diphenyl methane;

aliphatic aldehydes and their acetals such as e.g. hexanal; heptanal; octanal; nonanal; decanal; undecanal; dodecanal; tridecanal; 2-methyloctanal; 2-Methylnonanal; (E)-2-Hexenal; (Z)-4-Heptenal; 2,6-Dimethyl-5-heptenal; 10-Undecenal; (E)-4-Decenal; 2-Dodecenal; 2,6,10-Trimethyl-9-undecenal; 2,6,10-Trimethyl-5,9-undecadienal; heptanaldiethyl acetal; 1,1-Di methoxy-2,2,5-trimethyl-4-hexen; citronellyloxyacetaldehyd; 1-(1-Methoxy-propoxy)-(E/Z)-3-hexene;

aliphatic ketons and their oximes such as e.g 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

aliphatic sulphur containing compounds such as e.g. 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as e.g. 2-Nonenoic acid nitrile; 2-Undecenoic acid nitrile; 2-Tridecenoic acid nitrile; 3,12-Tridecadienoic acid nitrile; 3,7-Dimethyl-2,6-octadienoic acid nitrile; 3,7-Dimethyl-6-octenoic acid nitrile;

esters of aliphatic carbonic acids such as e.g. (E)- and (Z)-3-hexenyl formiate; ethylaceto acetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethylisovalerianate; ethyl-2-methyl pentanoate; ethyl hexanoate; allyl hexanoate; ethyl heptanoate; allyl heptanoate; ethyl octanoate; ethyl-(e,z)-2,4-decadienoate, particularly ethyl-2-trans-4-cis-decadienoate; methyl-2-octinate; methyl-2-noninate; allyl-2-isoamyloxyacetate; methyl-3,7-dimethyl-2,6-octadienoate; 4-methyl-2-pentyl-crotonate;

Formiates, Acetates, Propionates, Isobutyrates, Butyrates, Isovalerianates, Pentanoates, Hexanoates, Crotonates, Tiglinates or 3-Methyl-2-butenoates of acrylic terpene alcohols such as e.g. Citronellol; Geraniol; Nerol; Linalool; Lavadulol; Nerolidol; Farnesol; Tetrahydrolinalool; Tetrahydrogeraniol; 2,6-Dimethyl-7-octen-2-ol; 2,6-Dimethyloctan-2-ol; 2-Methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol;

acrylic terpene aldehydes and ketones such as e.g. geranial; neral; citronellal; 7-hydroxy-3,7-di methyloctanal; 7-methoxy-3,7-dimethyloctanal; 2,6,10-trimethyl-9-undecenal; geranylaceton as well as their dimethyl and diethyl acetales, particularly the dimethyl and diethyl acetals of geranial, neral, 7-hydroxy-3,7-di methyloctanal;

formiates, acetates, propionates, isobutyrates, butyrates, isovalerianates, pentanoates, hexanoates, crotonates, tiglinates and 3-methyl-2-butenoates of cyclic terpene alcohols such as e.g. menthol; isopulegol; alpha-terpineol; terpinenol-4; menthan-8-ol; menthan-1-ol; menthan-7-ol; borneol; isoborneol; linalooloxid; nopol; cedrol; ambrinol; vetiverol; guajol;

cyclic terpene aldehydes and ketones such as e.g. menthone; isomenthone; 8-mercaptomenthan-3-one; carvone; campher; fenchone; alpha-ionone; betaionone; alpha-n-methylionone; beta-n-methylionone; alpha-isomethylionone; beta-isomethylionone; alpha-iron; alpha-damascone; beta-damascone; betadamascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2h-2,4a-methanonaphthalen-8(5h)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedrylketone);

cyclic and cycloaliphatic ethers such as e.g. cineol; cedrylmethylether; cyclododecylmethylether; 1,1-dimethoxycyclododecan; (ethoxy-methoxy)cyclododecan; alpha-cedrenepoxid; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as e.g. 4-tert.-butyl-cyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

cycloaliphatic aldehydes such as e.g. 2,4-dimethyl-3-cyclohexencarbaldehyde; 2-methyl-4-(2,2,6-trimethyl-cyclohexen-1-yl)-2-butenal; 4-(4-hydroxy-4-methyl-pentyl)-3-cyclohexencarbaldehyde; 4-(4-methyl-3-penten-1-yl)-3-cyclohexencarbaldehyde;

cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

esters of cyclic alcohols such as e.g. 2-tert-Butylcyclohexyl acetate; 4-tert-Butylcyclohexyl acetate; 2-tert-Pentylcyclohexyl acetate; 4-tert-Pentylcyclohexyl acetate; 3,3,5-Trimethylcyclohexyl acetate; Decahydro-2-naphthyl acetate; 2-Cyclopentylcyclopentyl crotonate; 3-Pentyltetrahydro-2H-pyran-4-yl acetate; Decahydro-2,5,5,8a-tetramethyl-2-naphthyl acetate; 4,7-Methano-3a,4,5,6,7,7a-hexahydro-5, or, respectively, 6-indenyl acetate; 4,7-Methano-3a,4,5,6,7,7a-hexahydro-5, or, respectively, 6-indenyl propionate; 4,7-Methano-3a,4,5,6,7,7a-hexahydro-5, or, respectively 6-indenyl isobutyrate; 4,7-Methano-octahydro-5, or, respectively, 6-indenyl acetate;

esters of cycloaliphatic alcohols such as e.g. 1-Cyclohexylethyl crotonate;

esters of cycloaliphatic carbonic acids such as e.g. allyl-3-cyclohexyl propionate; allylcyclohexyloxy acetate; cis- and trans-methyldihydro jasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolan-2-acetate;

esters of araliphatic alcohols and aliphatic carbonic acids such as e.g. benzyl acetate; benzyl propionate; benzyl isobutyrate; benzyl isovalerianate; 2-phenylethyl acetate; 2-phenylethyl propionate; 2-phenylethyliso butyrate; 2-phenylethyliso valerianate; 1-phenylethyl acetate; alpha-trichlormethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers such as e.g. 2-Phenylethylmethylether; 2-Phenylethyl-isoamylether; 2-Phenylethyl-1-ethoxyethylether; Phenylacetalde-hyddimethyl acetal; Phenylacetaldehyddiethyl acetal; Hydratropaaldehyd-dimethyl acetal; Phenylacetaldehydglycerin acetal; 2,4,6-Trimethyl-4-phenyl-1,3-dioxane; 4,4a,5,9b-Tetrahydroindeno[1,2-d]-m-dioxin; 4,4a,5,9b-Tetrahydro-2,4-dimethylindeno[1,2-d]-m-dioxin;

aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl) propanal; 2-methyl-3-(4-tert.-butylphenyl)propanal; 2-methyl-3-(4-isobutylphenyl)propanal; 3-(4-tert.-butylphenyl)propanal; cinnamon aldehyde; alpha-butylzimtaldehyde; alpha-amylzimtaldehyde; alpha-hexylzimtaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylendioxybenzaldehyde; 3,4-di methoxybenzaldehyde; 2-methyl-3-(4-methoxyphenyl)propanal; 2-methyl-3-(4-methylendioxyphenyl) propanal;

aromatic and araliphatic ketones such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethylketone; 6-tert.-butyl-1,1-dimethyl-4-indanylmethylketone; 1-[2,3-dihydro-1,1,2,6-tetramethyl-3-(1-methylethyl)-1H-5-indenyl] ethanone; 5',6',7',8'-tetrahydro-3,5',5',6',8',8'-hexamethyl-2-acetonaphthone;

aromatic and araliphatic carbonic acids and their esters such as e.g. benzoic acid; phenylacetic acid; methyl benzoate; ethyl benzoate; hexyl benzoate; benzyl-benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethyl benzoate; ethyl-3-phenyl glycidate; ethyl-3-methyl-3-phenyl glycidate;

nitrogen containing aromatic compounds such as e.g. 2,4,6-trinitro-1,3-dimethyl-5-tert.-butylbenzol; 3,5-di-nitro-2,6-dimethyl-4-tert.-butyl acetophenone; cinnamic acid nitrile; 3-methyl-5-phenyl-2-pentenoic acid nitrile; 3-methyl-5-phenylpentanoic acid nitrile; methylanthranilate; methy-n-methylanthranilate; schiff base of methylanthranilate with 7-hydroxy-3,7-dimethyloctanal, 2-methyl-3-(4-tert.-butylphenyl)propanal or 2,4-dimethyl-3-cyclohexencarbaldehyde; 6-isopropyl-chinolin; 6-isobutylchinolin; 6-sec.-butylchinolin; 2-(3-phenylpropyl)pyridin; indol; skatol; 2-methoxy-3-isopropylpyrazine; 2-isobutyl-3-methoxypyrazine;

phenylethers and phenylesters such as e.g. estragol; anethol; eugenyl-methylether; isoeugenylmethylether; diphenylether; beta-naphthylmethylether; beta-naphthylethylether; beta-naphthylisobutylether; 1,4-dimethoxybenzol; eugenyl acetate; p-kresylphenyl acetate;

heterocyclic compounds such as e.g. 2,5-dimethyl-4-hydroxy-2h-furan-3-one; 2-ethyl-4-hydroxy-5-methyl-2h-furan-3-one; 3-hydroxy-2-methyl-4h-pyran-4-one; 2-ethyl-3-hydroxy-4h-pyran-4-one; and dihydrocumarin; octahydrocumarin; lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide;

11-oxa-1,16-hexadecanolide; 12-oxa-1,16-hexadecanolide; ethylen-1,12-dodecandioate; ethylen-1,13-tridecandioate; cumarin; 2,3-dihydrocumarin; octahydrocumarin.

So-called pro-drugs are also suitable as aromatic substance. This class of compounds includes compounds which release a desired aromatic substance molecule by breaking a chemical bond for example by hydrolysis. Typically, a desired aromatic substance raw material is chemically connected with a carrier, preferably a slightly volatile or moderately volatile carrier for producing a pro-drug. The combination results in a less volatile and more strongly hydrophobic pro-drug with improved attachment to cloth. The aromatic substance is then released by breaking the bond between the aromatic substance raw material and the carrier, for example by a change of the pH value (e.g. by transpiration when wearing), humidity, warmth and/or sunlight during the storage or drying on the clothesline.

Additionally or alternatively, one or more insect repellents may be contained, e.g. N,N-d-iethyl-m-toluamide, 1,2-pentandiol and/or ethyl butylacetylaminopropionate.

Additionally or alternatively, one or more cooling substances may be contained. Cooling substances are compounds which cause an impression of cold on the skin. Typically these are menthol compounds which—in addition to the basic structure menthol itself—are for example selected from the group consisting of menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamat, monomethyl succinate (FEMA GRAS 3810), monomethyl glutamate (FEMA GRAS 4006), menthoxy-1,2-propanediol (FEMA GRAS 3784), menthoxy-2-methyl-1,2-propandiol (FEMA GRAS 3849) as well as the menthane carbonic acid esters and amides WS-3, WS-4, WS-5, WS-12, WS-14 and WS-30 as well as their mixtures. A first important representative of these compounds is monomenthyl succinate (FEMA GRAS 3810). Succinate as well as the analogous monomenthyl glutarate (FEMA GRAS 4006) are important representatives of monomenthyl esters based on di- and polycarbonic acids:

Examples for the application of these substances are e.g. found in the documents WO 2003 043431 (Unilever) or EP 1332772 A1 (IFF).

The next important group of preferred menthol compounds in the sense of the invention comprises carbonate esters of menthol and polyols such as e.g. glycolene, glycerol or carbohydrates such as e.g. menthol ethylenglycol carbonate (FEMA GRAS 3805=Frescolat® MGC), menthol propylenglycol carbonate (FEMA GRAS 3784=Frescolat® MPC), menthol 2-methyl-1,2-propandiol carbonate (FEMA GRAS 3849) or the respective sugar derivatives. Also preferred are the menthol compounds menthyl lactate (FEMA GRAS 3748=Frescolat® ML) and particularly menthone glyceryl acetal (FEMA GRAS 3807) or, respectively, menthone glyceryl ketal (FEMA GRAS 3808), which is marketed as Frescolat® MAG. Particularly preferably among these substances are menthone glyceryl acetal/ketal as well as menthyl lactate as well as menthol ethylene glycol carbonate or, respectively, menthol propylene glycol carbonate which are marketed by the applicant as Frescolat® MGA, Frescolat® ML, Frecolat® MGC and Frescolat® MPC. In the 70ies of the last century, menthol compounds were first developed which have a c-c-bond in the 3-position and out of which also a plurality of representatives may be used. These substances are typically designated as WS-types. Basic structure is a menthol derivative in which the hydroxyl group is replaced by a carboxyl group (WS-1). All further WS-types are derived from this structure, such as for example the preferred species WS-3, WS-4, WS-5, WS-12, WS-14 and WS-30.

Additionally or alternatively one or more substances may be used which are known as TRPV1 and TRPV3 modulators by the skilled person. Examples of such substances are Vanillyl derivatives, preferably vanillylether, capsaicin, allyl isothiocyanate, gingerol, menthoxymethyl)-2-phenyl-1,3-dioxolan, 4-(I-menthoxymethyl)-2-(3',4'-dihydroxyphenyl)-I,3-dioxolan, 4-(I-menthoxymethyl)-2-(2'-hydroxy-3'-methoxyphenyl)-3-dioxolan, menthoxymethyl)-2-(4'-methoxyphenyl)-3-dioxolan, 4-(I-menthoxymethyl)-2-(3',4'me-thylene-dioxyphenyl)-3-dioxolan, 4-(I-menthoxymethyl)-2-(3'-methoxy-4'-hydroxyphenyl)-3-dioxolan, red pepper oil, red pepper oleoresin, ginger oleoresin, nonylic acid vanillyl amide, jambu oleoresin, zanthoxylum piperitum extract, sanshool I, sanshool II, sanshoamide, black pepper extract, chavicines and further substances as they are mentioned for example in the document U.S. Pat. No. 6,780,443.

Additionally or alternatively one or more flavours, one or more cosmetic ingredients, one or more pharmaceutically active substances, one or more latent heat accumulators, one or more adsorbents and/or one or more ingredients for oral and dental care agents may be contained.

As a result, in a method according to the invention, preferably in an embodiment classified as preferred above, preferably several or all of the capsules (K) contain one or more ingredients from the group consisting of aromatic substances, flavours, cosmetic ingredients, pharmaceutically active substances, insect repellents, ingredients for oral and dental care agents, latent heat accumulators and adsorbents.

In a preferred embodiment of the method according to the invention, preferably in an embodiment classified as preferred above, several or all capsules (K) have a wall material comprising or consisting of or based on one or more of the substances selected from the group consisting of naturally, semi-synthetic and fully synthetic shell materials, preferably of melamine formaldehyde resins, gelatin, alginates, polyurethans, polyamides and polycarbamides.

Preferably, the capsules provided in step (i) have a capsule wall of a material suitable for the desired purpose of use. Suitable as capsule wall material may be e.g. natural shell materials such as gum Arabic, agar-agar, agarose, maltodextrins, alginic acid or, respectively, its salts, e.g. sodium or calcium alginate, fats and fatty acids, cetyl alcohol, collage, chitosan, lecithins, gelatin, albumin, shellac, polysaccharides such as starch or dextran, polypeptides, protein hydrolysates, sucrose and waxes, semi-synthetic shell materials such as among others chemically modified celluloses, particularly cellulose esters and ethers, e.g. cellulose acetate, ethyl cellulose, hydroxypropyl cellulose, hydroxypropylmethyl cellulose and carboxymethyl cellulose as well as starch derivatives, particularly starch ethers and esters or fully synthetic shell materials for example polymers such as polyacrylates, polyamides, polyvinylalcohol, aminoplastes, phenoplastes or polyvinylpyrrolidone.

Capsules (K) which may be used for the purpose of the present invention are commercially obtainable e.g. the following commercial products (the shell material is indicated in brackets) Hallcrest Microcapsules (gelatin, gum arabicum), Coletica Thalaspheres (maritime collagen), Lipotec Millicapssules (alginic acid, agar-agar), Induchem Unispheres (lactose, microcrystalline cellulose, hydroxypropylmethyl-cellulose); Unicerin C30 (lactose, microcrystalline cellulose, hydroxypropylmethylcellulose), Kobo Glycospheres (modified starch, fatty acid ester, phospholipids), Softspheres (modified agar-agar) and Kuhs Probiol Nanospheres (phospholipids) as well as Primaspheres and Primasponges (chitosan, alginate) and Primasys (phospholipids) as well as capsules of synthetic polymers Micronal® (BASF), microcapsules 500 and 560 (Koehler SE), Folco Smart-Caps®, Enfinit™, Ensensa. Alternatively, the capsules (K) can be produced themselves, preferably taking into account the above described preferred shell materials and ingredients. Suitable methods therefore are known to a skilled person, e.g. by surface polymerization (e.g. J. Li, A. P. Hitchcock, H. D. H Stover, I. Shirley; Macromolecules; 2009; 42; 2428-2432) or in-situ polymerization (such as e.g. DE19835114A1).

According to a preferred embodiment of the present invention, the capsules (K) are provided in form of a capsule dispersion for further use in a method according to the invention (as described herein). Such dispersion may be produced by dissolving a substance crystallisable from a solution in a suitable solvent. Subsequently, the capsules are added and conditions are adjusted by which the dissolved substance crystallizes again.

In a preferred embodiment of the method according to the invention the, one, more or all solvents is/are selected from the group consisting of water and solvents which can be mixed with water, preferably ethanol, isopropanol, acetone and DMSO.

It is particularly advantageous to select such solvents in which the crystallisable material(s) crystallize particularly well.

In a method according to the invention, particularly in a preferred embodiment, the, one, more or all crystallisable material(s) can by crystallized in a solvent which can be mixed with water or in water and/or is/are preferably selected from the group consisting of salts, preferably alkali salts and alkaline earth salts, particularly preferably sodium salts, particularly preferably sodium sulfate, sodium chloride or sodium carbonate, sugars and urea.

Particularly preferred are soluble salts, sugar or urea as they can be particularly well dissolved in for example water or liquids which can be mixed with water and as they easily release the contained capsules (K) at the use according to the invention.

In a method according to the invention, preferably in an embodiment classified as preferred above, the solvent(s) is/are heated in step (ii), if present, to a temperature in the range of from 23 to 50° C., preferably in a range of from 25 to 40° C., particularly preferably in a range of from 30 to 35° C.

In case the solvent(s) is/are heated to such a temperature, the crystallisable material(s) dissolve particularly well or, respectively, particularly fast in the solvent(s).

Preferably, in a method according to the invention, preferably in an embodiment classified as preferred above, step (iii) comprises a stirring to dissolve the crystallisable material(s) in the solvent(s) or to facilitate the same, preferably with a stirring speed in a range of from 100 to 1,871 rotations/min [U/min], preferably in a range of from 500 to 1300 rotations/min [U/min], particularly preferably in a range of from 1000 to 1200 rotations/min [U/min]; preferably by means of a jet stream mixer.

In a preferred embodiment of the method according to the invention, preferably in an embodiment classified as preferred above, the temperature of the mixture (M1) is reduced to a temperature of <20° C. preferably <15° C., further preferably <10° C., particularly preferably <5° C. in step (vi), wherein the reduction of the temperature is preferably applied within a time frame in the range of from 0.25 to 3 hours, preferably 0.5 to 2 hours, particularly preferably within a time frame of from 0.75 to 1.5 hours.

Advantageously, the crystallization of the crystallisable material(s) occurs at the temperatures and the time frame described above. When the reduction of the temperature is applied within a time frame in the ranges described above, the crystallization of the crystallisable material(s) occurs at particularly advantageous conditions and results in the formation of structures enabling a particularly beneficial inclusion of the capsules (K) containing one or more ingredients into the forming crystals, which results in a good protection of the capsules (K) from for example grinding by arising shear forces when used according to the invention.

Preferably, step (vii) of the method according to the invention, preferably in an embodiment classified as preferred above, comprises or consists of one, two or all of the following steps:
  decanting the solvent(s),
  separating (e.g. by filtering or centrifuging) the crystals,
  drying the mixture (M2) obtained in step (vi) and/or the filtered crystals,
  to obtain a powder comprising or consisting of a plurality of capsules (K) enclosed in crystals and containing one or more ingredients.

By means of the preferred decanting and/or filtering and/or drying in step (vii), a powder according to the invention is obtained which can be particularly advantageously added to or, respectively mixed with different liquid or solid products due to its powder form.

In a method according to the invention, particularly in a preferred embodiment, the weight ratio of the total amount of solvent(s) to the total amount of crystallisable material(s) to the total amount of capsules (K) and/or capsule dispersion (cf. above) is in the following range in step (i): 1-10:0.5-5: 0.1-3, preferably in the following range: 3-7:1-3:0.5-2.

The ranges of the weight ratios mentioned above are particularly advantageous as in these ranges an amount of crystallisable material(s) particularly advantageous for the crystallization process is present in the solvent(s) and the forming crystals can incorporate a particularly advantageous amount of capsules (K) such that an amount of capsules (K) particularly advantageous for the use according to the invention is present in the resulting powder, whereas no unnecessary loss of capsules (K) occurs in the production of the same.

A further aspect of the present invention relates to a powder comprising or consisting of a plurality of capsules enclosed in crystals and containing one or more ingredients, preferably produced or producible by a method according to the invention, preferably in a preferred embodiment.

What was said above with regard to a method according to the invention also applies accordingly for preferred embodiments of such a powder, particularly what was said with regard to preferred embodiments, especially particularly with regard to the capsules to be (preferably) used according to the invention, their shell materials and ingredients as well as the crystallisable materials to be (preferably) used.

As mentioned above, the crystals or, respectively, a powder each produced according to the invention can advantageously be mixed with a washing powder formulation or, respectively typical components of a washing powder without problems. But also other products may contain the crystals or, respectively, powders described herein.

Thus a further aspect of the present invention relates to a product selected from the group consisting of washing and cleaning agents, body care products, compositions serving for food or pleasure, cosmetic or pharmaceutical compositions, perfumed or perfuming products or products to be perfumed, preferably rimblocks, wherein the product comprises a powder according to the invention.

In addition to a powder as described herein, such products also contain the further ingredients typical and suitable for such products. These are well known to a skilled person on the respective field and are selected depending on the desired application.

Products according to the invention thus preferably also contain one or more typical components or, respectively, ingredients of washing and cleaning agents, body care products, compositions serving for food or pleasure, cosmetic or pharmaceutical compositions, perfumed or perfuming products or products to be perfumed.

Further, an aspect of the present invention relates to the use of a powder according to the invention, wherein several or all of the capsules (K) contain one or more ingredients of the group selected from cooling agents, aromatic substances (preferably as described above) and flavours, preferably in an amount sufficient for imparting a cooling effect and/or for imparting, modifying or enhancing a sensory, preferably olfactory and/or gustatory, impression, for imparting, modifying or enhancing a sensory impression, preferably an olfactory and/or gustatory impression, or for perfuming a product, preferably a product according to the invention.

A further aspect of the present invention relates to a method for producing a product according to the invention, comprising or consisting of the following steps:
 (a) providing
  (a.1) a powder according to the invention as well as
  (a.2) one or more further components, preferably one or more further components or, respectively, ingredients of washing and cleaning agents, body care products, compositions serving for food or pleasure, cosmetic or pharmaceutical compositions or perfumed or perfuming products or products to be perfumed and
 (b) mixing the components (a.1) and (a.2).

A further aspect of the present invention relates to a method for perfuming substrates, preferably hair, skin, leather or textile fibres, comprising or consisting of the following steps:
 (a) providing a powder or product according to the invention as described herein, wherein several or all of the capsules (K) contain one or more ingredients of the group consisting of aromatic substances (preferably as described above) and flavours, preferably in an amount sufficient for imparting, modifying or enhancing a sensory impression, preferably an olfactory and/or gustatory impression and
 (b) applying the powder or, respectively, product onto the substrate(s) to be perfumed, preferably hair or, respectively, skin or, respectively, fibres or, respectively, leather, preferably, with regard to the capsules (K) contained therein, in a sensorically effective amount, preferably in an amount sufficient for a consumer to perceive one or more olfactory or gustatory scents.

What was said above with regard to the further aspects of the present invention applies accordingly to preferred embodiments of the uses and methods described above, particularly what was said with regard to preferred embodiments, especially particularly with regard to the capsules to be (preferably) used, their shell materials and ingredients as well as the crystallisable materials to be (preferably) used.

In the following, the invention is further described by means of selected examples. As far as not stated otherwise, all indications refer to the weight.

EXAMPLE 1 (ACCORDING TO THE INVENTION)

450 g of water are warmed to approximately 33° C. Subsequently, 200 g of sodium sulfate are dissolved by stirring and slowly cooled. When the crystallization initiates, 150 g capsule dispersion (710544 Symcap Tomcap, Symrise) are added and cooled to approximately 2° C. and subsequently the precipitation is filtered. The filter cake is then dried.

EXAMPLE 2 (ACCORDING TO THE INVENTION)

450 g of water are warmed to approximately 40° C., then 167 g sodium carbonate are added and dissolved while stirring. Subsequently 150 g capsule dispersion (710544 Symcap Tomcap, Symrise) and further 50 g of water are added. Subsequently it is cooled to 1.0° C. After filtering, the filter residue is dried.

EXAMPLE 3 (ACCORDING TO THE INVENTION)

250 g of water are warmed to approximately 37° C. and subsequently 200 g sodium acetate are dissolved while stirring. Subsequently the mixture is cooled to 26° C. and when the crystallization initiates, 150 g capsule dispersion (710544 Symcap Tomcap, Symrise) are added and cooled to 1.7° C. within approximately 1 hour. Afterwards, the precipitation is filtered and the filter cake is dried at room temperature.

EXAMPLE 4 (ACCORDING TO THE INVENTION)

A mixture of 330 g water, 206 g modified corn starch (Capsul, Ingredion), 27.0 g maltose monohydrate, 17.5 g luviskol K-30 and 150 g capsule dispersion (710544 Symcap Tomcap, Symrise) are spray dried (inlet temperature 190° C., outlet temperature 90° C.) in a spray dryer (Büchi B 290).

EXAMPLE 5 (ACCORDING TO THE INVENTION)

450 g of water are warmed to approximately 80° C. Then, 450 g urea are dissolved while stirring. Subsequently 150 g capsule dispersion (710544 Symcap Tomcap, Symrise) are added, subsequently it is cooled to room temperature and the precipitation is filtered. The filter cake is subsequently dried.

EXAMPLE 6 (ACCORDING TO THE INVENTION)

500 g of water are warmed to approximately 40° C. Then 100 g sodium sulfate are dissolved while stirring. Subsequently 20 g of capsule dispersion (710544 Symcap Tomcap, Symrise) are added, subsequently cooled to 25° C. Afterwards, the mixture is further cooled to approximately 1.7° C. and the further 20 g sodium sulfate are added as seed crystal and the arising precipitation is filtered. The filter cake is subsequently dried.

EXAMPLE 7 (COMPARISON)

Figure 2:
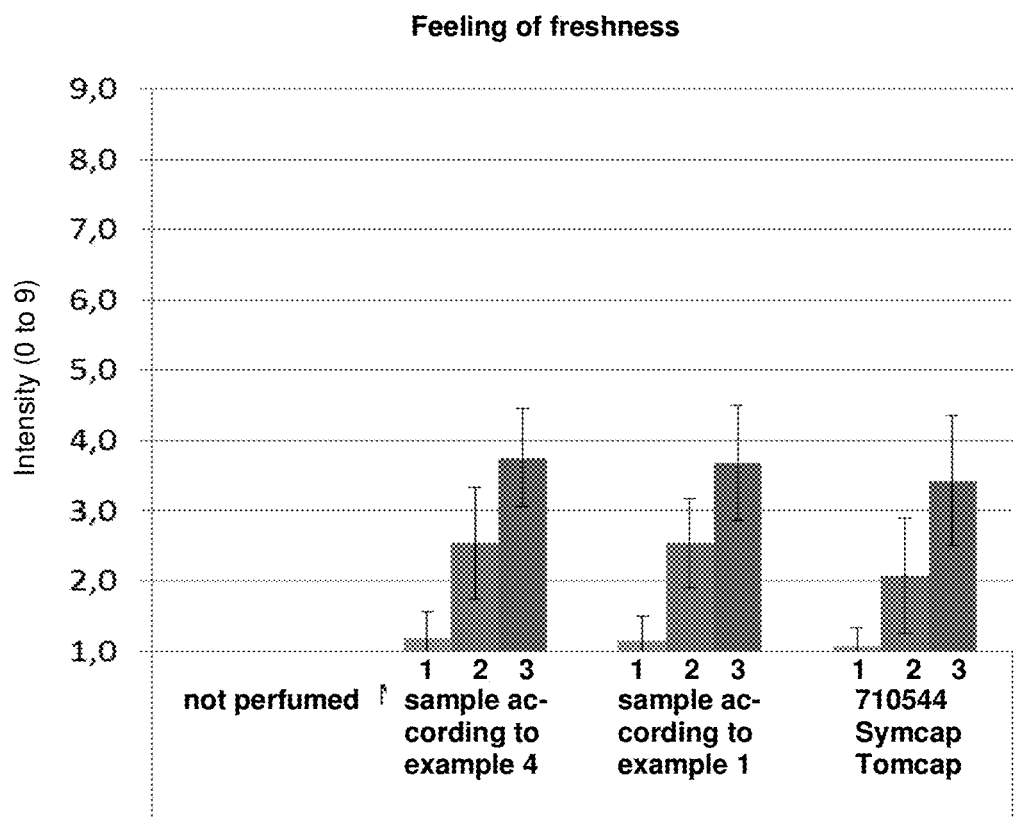
FIG. 2 shows the intensity of the release of ingredients for inventive capsules (K), spray dried capsules, and a liquid capsule dispersion.

For preparing a sensory comparison, each, 0.200 g sample according to example 4, 0.207 g sample according to example 1 were added to 40 g washing powder and 0.08 g 710544 Symcap Tomcap (Symrise AG, Holzminden, Germany) were added to 40 g washing powder (Denk mit Vollwaschmittel Ultra Sensitive Pulver, dm-drogerie markt GmbH+Co. KG, Karlsruhe, Germany) and were mixed. Subsequently, the samples obtained in this way were washed on 2 kg terry cloth each (Fa. Karl Heinz Hesse GmbH, Dransfeld, Germany, Waschlappen TB1, 80% BW, 20% PES, 30×30 cm) in a standard European washing machine at 40° C. Subsequently, the terry cloths were dried on the line at room temperature. The anonymised samples were then smelled by a panel of 14 experts each without mechanical stress (untreated), after soft kneading of the laundry (kneaded) and after rubbing the cloths with each other (rubbed) and the intensity of the smell was evaluated on a scale ranging from 1 to 9. The result (cf. FIG. 2) shows that the release of the capsules or, respectively, of their ingredients in the washing powder, produced by the method according to the invention, compared with spray dried capsules (according to example 4) or in comparison with the use of liquid capsule dispersion alone (710544 Symcap Tomcap) is not reduced.

EXAMPLE 8 (ACCORDING TO THE INVENTION)

500 g of water are warmed to approximately 33° C. Then, 200 g of sodium sulfate are dissolved while stirring. Subsequently, the mixture is cooled slowly, the crystallisation initiates and first small crystals are forming. Then 198 g of Folco Microdeur (Follmann GmbH & Co. KG, Minden, Germany) are added and it is cooled to 1.7° C. Subsequently, the precipitation is filtered and the filter cake is dried.

The invention claimed is:

1. A method for producing a powder, wherein the powder comprises capsules (K) enclosed in crystals and the capsules (K) include one or more ingredients, the method comprising:
   (i) providing one or more solvents, one or more crystallisable materials, and capsules (K) containing the one or more ingredients,
   (ii) optionally, increasing the temperature of the one or more solvents,
   (iii) adding (iii.1) the one or more crystallisable materials and (iii.2) optionally, the capsules (K) before, after, or simultaneously with the crystallisable materials, to the one or more solvents and dissolving the one or more crystallisable materials in the one or more solvents to obtain a mixture (M1),
   (iv) reducing the temperature of the mixture (M1) to a temperature below or even with the crystallization temperature of the one or more crystallisable materials,
   (v) adding the capsules (K) or, respectively, further capsules (K), wherein (v) is optional in case (iii.2) is applied,
   (vi) further reducing the temperature of the mixture (M1) to obtain a mixture (M2) comprising capsules (K) enclosed in crystals and containing one or more ingredients, wherein the mixture (M2) is cooled to a temperature resulting in the precipitation of the capsules (K) enclosed in crystals and containing the one or more ingredients, without spray drying; and
   (vii) collecting the precipitated crystals to obtain the powder of capsules (K) enclosed in crystals containing the one or more ingredients, and not a liquid capsule dispersion.

2. The method according to claim 1, wherein at least one of the one or more solvents are selected from water and solvents which can be mixed with water.

3. The method according to claim 1, wherein at least one of the one or more crystallisable materials can be crystallized in a solvent which can be mixed with water or in water and/or is/are selected from salts.

4. The method according to claim 1, wherein several or all of the capsules (K) contain one or more ingredients selected from aromatic substances, flavours, cosmetic ingredients, pharmaceutically active substances, insect repellents, ingredients for oral and dental care, and adsorbents.

5. The method according to claim 1, wherein several or all capsules (K) have a wall material comprising one or more substances selected from natural, semi-synthetic, and fully synthetic shell materials.

6. The method according to claim 1, wherein the one or more solvents are heated in (ii), if present, to a temperature in the range of from 23 to 50° C.

7. The method according to claim 1, wherein (iii) comprises stirring to dissolve the one or more crystallisable materials in the one or more solvents or to facilitate the same.

8. The method according to claim 1, wherein the temperature of the mixture (M1) is reduced to a temperature of <20° C. in (vi), wherein the reduction of the temperature is applied within a time frame in the range of from 0.25 to 3 hours.

9. The method according to claim 1, wherein (vii) comprises at least one of the following:
   decanting the one or more solvents,
   separating the crystals, and
   drying the mixture (M2) obtained in (vi) and/or the filtered crystals to obtain a powder comprising a plurality of capsules (K) enclosed in crystals and containing the one or more ingredients.

10. The method according to claim 1, wherein the weight ratio of the total amount of the one or more solvents to the total amount of the one or more crystallisable materials to the total amount of capsules (K) in (i) is 1-10:0.5-5:0.1-3.

11. The method according to claim 3, wherein at least one of the one or more crystallisable materials are alkali salts, alkaline earth salts, sodium salts, sodium sulfate, sodium chloride, sodium carbonate, sugars, urea, or a combination thereof.

12. The method of claim 5, wherein the wall material of several or all of the capsules (K) comprises one or more substances selected from melamine formaldehyde resins, gelatin, alginates, polyurethans, polyamides, and polycarbamides.

13. The method of claim 7 comprising stirring at a speed of 100 to 1,871 rotations/min (U/min).

* * * * *